US005952200A

United States Patent [19]
Johnson et al.

[11] Patent Number: 5,952,200
[45] Date of Patent: Sep. 14, 1999

[54] METHOD OF DIAGNOSING CANCER IN HUMAN CELLS USING A REVERSE TRANSCRIPTASE-POLYMERASE CHAIN REACTION FOR IDENTIFYING THE PRESENCE OF STROMELYSIN-3

[75] Inventors: Lewis D. Johnson; Maurice Nachtigal; Margaret Hunt, all of Columbia, S.C.

[73] Assignee: University of South Carolina, Columbia, S.C.

[21] Appl. No.: 08/796,362

[22] Filed: Feb. 6, 1997

[51] Int. Cl.$^6$ .............................. C12P 19/34; C12Q 1/68; C07H 21/02; C07H 21/04
[52] U.S. Cl. ......................... 435/91.2; 435/6; 435/91.21; 435/91.51; 536/23.1; 536/24.3; 536/24.31; 536/24.33
[58] Field of Search .......................... 435/6, 91.2, 91.21, 435/91.51; 935/8, 77, 78; 536/23.1, 24.3, 24.33, 24.31

[56] References Cited

U.S. PATENT DOCUMENTS

| | | | |
|---|---|---|---|
| 4,683,188 | 7/1987 | Suzuki et al. | 430/110 |
| 4,683,195 | 7/1987 | Mullis et al. | 435/6 |
| 4,683,202 | 7/1987 | Mullis et al. | 435/91 |
| 5,075,216 | 12/1991 | Innis et al. | 435/6 |

OTHER PUBLICATIONS

Basset et al Nature 348:699–704 (Dec. 1990).

Foley et al Trends in Genetics 9:380–385 (Nov. 1993).

Muer et al. Cancer Research 53:165–169 (Jan. 1993).

Anderson et al 55:4120–4126 (Sep. 1995).

Porte et al Int. J. Cancer 64:70–75 (Feb. 1995).

DeCosse Cancer 62:1787–1790 (Oct. 1988).

Johnson et al. Human Pathology 27:964–968 (Sep. 1996).

Yamagata S. Yoshii et al., "Occurrence of an active form of gelatinase in human gastric and colorectal carcinoma tissues," Cancer Letters, 59(1):51–5, Jul. 26, 1991; Abstract only.

S. McDonnell et al., "Expression and localization of the matrix metalloproteinase pump–1 (MMP–7) in human gastric and colon carcinomas," Molecular Carcinogenesis, 4(6):527–33, 1991; Abstract only.

Richard Poulsom et al., "Stromal Expression of 72 kda Type IV Collagenase (MMP–2) and TIMP–2 mRNAs in Colorectal Neoplasia," American Journal of Pathology, vol. 141, No. 2, Aug. 1992, pp. 389–396.

Robert E. Hewitt et al., "Distribution of Collagenase and Tissue Inhibitor of Metalloproteinases (TIMP) in Colorectal Tumours," Int. J. Cancer: 49, 666–672, 1991.

Anna T. Levy et al., "Increased Expression of the M–72,000 Type IV Collagenase in Human Colonic Adenocarcinoma," Cancer Research 51, Jan. 1, 1991, pp. 439–444.

A. van den Hooff, "Stromal Involvement in Malignant Growth," Advances in Cancer Research, vol. 50, pp. 159–195 (1988).

"Northern and Southern Blotting Facilitate Hybridization with Electrophoretically Separated Nucleic Acid Molecules," Molecular Biology of the Cell, Third Edition, 1994, pp. 301–303.

J. T. Davies, "In situ hybridization," Immunocytochemistry, pp. 177–178, 1993.

Matthlas Höss et al., "Excrement analysis by PCR," Nature, vol. 359, Sep. 17, 1992, p. 199.

David Sidranski et al., "Identification of ras Oncogene Mutations in the Stool of Patients with Curable Colorectal Tumors," Science, vol. 256, Apr. 3, 1992, pp. 102–105.

Isaiah J. Fidler et al., "Genetic Control of Cancer Metastasis," Journal of the National Cancer Institute, vol. 82, No. 3, Feb. 7, 1990, pp. 166–168.

Lance A. Liotta et al., "Cancer Metastasis and Angiogenesis: An Imbalance of Positive and Negative Regulation," Cell, vol. 64, Jan. 25, 1991, pp. 327–336.

Catherine Wolf et al., "Breast–Cancer–Associated Stromelysin–3 Gene Is Expressed in Basal Cell Carcinoma and During Cutaneous Would Healing," The Journal of Investigative Dermatology, vol. 99, No. 6, 1992, pp. 870–872.

S. J. Urbanski et al., "Expression of metalloproteinases and their inhibitors in primary pulmonary carcinomas," Br. Y Cancer, 66, 1992, pp. 1188–1194.

S. J. Urbanski et al., "Expression Pattern of Metalloproteinases and Their Inhibitors Changes with the Progression of Human Sporadic Colorectal Neoplasia," Dignostic Molecular Pathology, 2(2), 1993, pp. 81–89.

Quin Chou et al., "Prevention of pre–PCR mispriming and primer dimerization improves low–copy–number amplifications," Nucleic Acids Research, vol. 20, No. 7, pp. 1717–1723, (1992).

D. Margaret Hunt et al., "Amino Acid Changes in the L Polymerase Protein of Vesicular Stomatitis Virus Which Confer Aberrant Polyadenylation and Temperature–Sensitive Phenotypes," Virology 193, 1993, pp. 786–793.

Pirkko Huhtala et al., "Complete Structure of the Human Gene for 92–kDa Type IV Collagenase," Journal of Biological Chemistry, vol. 266, No. 25, Sep. 5, 1991, pp. 16485–16490.

Patrick Anglard et al., "Structure and Promoter Characterization of the Human Stromelysin–3 Gene," The Journal of Biological Chemistry, vol. 270, No. 35, Sep. 1, 1995, pp. 20337–20344.

Olivier Lefebvre et al., "The Breast Cancer–associated Stromelysin–3 Gene is Expressed During Mouse Mammary Gland Apoptosis," The Journal of Cell Biology, vol. 119, No. 4, Nov. 1992, pp. 997–1002.

(List continued on next page.)

*Primary Examiner*—Jeffrey Fredman
*Attorney, Agent, or Firm*—Dority & Manning, P.A.

[57] ABSTRACT

The present invention provides a sensitive test for objectively diagnosing the presence of cancerous cells in samples of human tissue, fluids, or semi-fluids, such as feces. The detection method employs the detection of transcripts for stromelysin-3 in human cells. A reverse transcriptase-polymerase chain reaction is utilized so that cancer can be detected in very small samples.

15 Claims, No Drawings

OTHER PUBLICATIONS

Akiko Okada et al., "Membrane–type matrix metalloproteinase (MT–MMP) gene is expressed in stromal cells of human colon, breast, and head and neck carcinomas," Proc. Natl. Acad. Sci. USA, vol. 92, Mar. 1995, pp. 2730–2734.

William H. Rodgers et al., "Patterns of Matrix Metalloproteinase Expression in Cycling Endometrium Imply Differential Functions and Regulation by Steroid Hormones," The American Society for Clinical Investigation, Inc., vol. 94, Sep. 1994, pp. 946–953.

Ken J. Newell et al., "Expression and Localization of Matrix–Degrading Metalloproteinases During Colorectal Tumorigenesis," Molecular Carcinogensis, vol. 10, 1994, pp. 199–206.

Duanging Pei et al., "Hydrolytic Inactivation of a Breast Carcinoma Cell–derived Serpin by Human Stromelysin–3," The Journal of Biological Chemistry, vol. 269, No. 41, Oct. 14, 1994, pp. 25849–25855.

Duanqing Pei et al., "Furin–dependent intracellular activation of the human stromelysin–3 zymogen," Nature, vol. 375, May 18, 1995, pp. 244–247.

PCR Product Labeling Sheet (1992).

RNAgent® Total RNA Isolation System Data Sheet (1992).

Leslie A. Wainwright et al., "Paraffin Beads Can Replace Mineral Oil as an Evaporation Barrier in PCR," Biotechniques, vol. 14, No. 1, 1993, pp. 35–36.

METHOD OF DIAGNOSING CANCER IN HUMAN CELLS USING A REVERSE TRANSCRIPTASE-POLYMERASE CHAIN REACTION FOR IDENTIFYING THE PRESENCE OF STROMELYSIN-3

FIELD OF THE INVENTION

The present invention is directed to the field of diagnostic tests for detecting the presence of cancerous cells in humans. More specifically, the present invention provides a method by which cancerous cells may be objectively detected by determining whether stromelysin-3 is present in the cells obtained from human tissues or fluids.

BACKGROUND OF THE INVENTION

Cancer is one of the deadliest diseases in the world today. Cancer generally refers to one of a group of more than 100 diseases that are caused by the uncontrolled growth and spread of abnormal cells. Unlike normal cells which reproduce until maturation is attained and then only reproduce as necessary to replace wounded cells, cancerous cells grow and divide endlessly, crowding out nearby cells and eventually spreading to other parts of the body.

The most common sites in which cancer develops include the skin, lungs, female breasts, colon, rectum, uterus, blood-forming tissues, and lymphatic system. Cancerous cells that have developed at one of these sites will grow rapidly into a malignant tumor, invading and destroying nearby tissues. Malignant cancerous tumors will eventually metastasize, or spread to other parts of the body, unless their progression is stopped.

Cancers are easier to treat and cure if they are discovered and treated prior to metastasis. Once cancerous cells metastasize by leaving a tumor, they will travel through the bloodstream or lymphatic system to other parts of the body, where the cells begin multiplying and developing into new tumors. It is this spreading of cancerous cells (also known as tumor progression) that makes cancer dangerously fatal. Although there have been great improvements in diagnosis, general patient care, surgical techniques, and local and systemic adjuvant therapies, most deaths from cancer are still due to metastases that are resistant to conventional therapies.

Despite the resistance of certain cancers to treatment, early detection methods have been utilized to identify cancerous cells so that current treatments can be used to slow and, in many cases, completely halt cancerous tumor progression. The chances of survival for patients with malignant forms of cancers increase greatly when the cancerous cells are detected at an early stage. Conventional techniques, such as surgical removal, chemotherapy, and radiation, can often be utilized to provide a full recovery if the cancer is caught at an early stage.

Most diagnostic methods depend on microscopic observation of tissue that has been removed from the body during a biopsy or other tissue removal procedure. For example, if cancer of the colon is suspected, a colonoscope is used to enter the large intestine and remove a sample of tissue. That sample is then sent to the pathology laboratory which will then determine the presence of abnormal cellular structure which would lead to a conclusion of cancerous cells.

Such current methods are very invasive in that they require surgical removal of tissue for analysis. It would be advantageous if less invasive tests could be developed. In addition, such analyses are, obviously, subjectively dependent upon the ability of the personnel performing the determinations. One major disadvantage of current methods is that the pathological analysis is sometimes initially equivocal, which results in performing additional surgical procedures to obtain sufficiently large samples of tissue for further diagnosis. It would also be advantageous if methods could be developed that are objective and that are based on relatively small tissue samples. Such methods could be used to either complement currently used subjective methods or vice versa.

Recently, various objective analyses that depend on DNA studies have been developed and are being pursued and approved for cancer detection. The detection of cancerous cells under such objective analyses often depends on an understanding of the molecular mechanisms involved in metastasis.

The following mechanisms are important to an understanding of the applicability of the present inventive diagnostic test which involves extracting RNA and then forming complementary DNA. The invasion by malignant cancerous cells of adjacent fibroconnective tissue and subsequent metastasis is a multi-stage process in which the degradation of the extracellular matrix surrounding the tumor is an essential step in allowing invasion of neoplastic cells. If the basement membrane integrity in cancerous tumors, such as colorectal and breast carcinomas is breached, then there is an increased probability of metastasis.

The secreted proteinases, including the matrix metalloproteinases, play a very important role in the progression of a number of malignant tumors in several tissues, including the colon, and are expressed at the initiation of invasion and at metastasis. The enzymes associated with invasive cancer are frequently localized to the stroma (which is quantitatively and qualitatively different around a cancer when compared to that beneath normal tissue). The enzymes degrade components of the extracellular matrix including those of the basement membrane. Understanding of this stage in the development of cancers is important as tumor cell interaction with the basement membrane is central to tumor invasion and is the step just preceding initiation of the metastatic cascade.

The matrix metalloproteinases are a group of endopeptidases involved in this process. They are subdivided into interstitial collagenases, stromelysins and type IV collagenases. A recent addition to the stromelysin group is metalloproteinase-11 (or stromelysin-3) which was first identified in the stromal cells of breast carcinoma, but which has now been found in the stroma of invasive basal cell carcinoma, peritumoral fibroblasts of squamous cell carcinomas of the head and neck, carcinoma of the lungs, and colon carcinoma. The expression of these identifiable metalloproteinases in the stromal cells of certain malignant tumors has been found to indicate a cancerous invasion of the surrounding tissue.

Previously, the expression of stromelysin-3 has been analyzed in a variety of carcinomas using primarily in-situ hybridization or Northern blotting techniques. In-situ hybridization involves the creation of complementary DNA clones synthesized after isolation of an individual gene or gene transcript. Northern blotting, on the other hand, involves the hybridization of a specific nucleic acid probe to messenger RNA which has been isolated from homogenized tissue, separated by electrophoretic methods, and transferred to a stable matrix such as nylon.

While Northern blotting and in-situ hybridization have been used to identify the presence of stromelysin-3 in cancerous cells, a reverse transcriptase-polymerase chain reaction technique has not been heretofore involved in such an identification. Reverse transcriptase-polymerase chain reaction has been used only as a means to clone stromelysin-3 in order to produce large amounts of the enzyme itself instead of being used as an identifying diagnostic test. In this particular prior use, the primers utilized were not those utilized here and the resulting product was not intended for identification purposes as in the present invention.

Polymerase chain reactions have also been utilized in the past to amplify the genomic DNA for stromelysin-3. However, no reverse transcriptase procedure was used that employed transcribing the complementary DNA. Instead, these previous uses employ RNA directly in hybridization processes such as Southern blotting.

The present invention overcomes some of the deficiencies of prior cancer detection methods by allowing an objective analysis to be conducted on cells taken from a relatively small sample of human tissue. In certain embodiments, the present invention allows for the non-invasive diagnosis of cancerous cells.

SUMMARY OF THE INVENTION

It is an object of the present invention to provide a diagnostic test for determining the presence of cancerous cells in humans.

It is an object of the present invention to provide a diagnostic test for cancer that is cost effective and highly sensitive.

It is a further object of certain embodiments of the present invention to provide a non-invasive diagnostic test for determining the presence of cancer in the human body.

It is a further object of certain embodiments of the present invention to provide a diagnostic test for detecting the presence of cancerous cells by examining bodily excretions.

The present method for detecting cancer depends on identifying the presence of the messenger RNA for the enzyme, stromelysin-3 (also known as matrix metalloproteinase-11), in cells taken from human tissue, human fluids or semi-fluids such as feces. The detection method utilizes the technique of reverse transcriptase-polymerase chain reaction whereby messenger RNA is extracted from human cells and is then transcribed (or copied) into the complementary DNA for stromelysin-3. The diagnostic test searches for enhanced transcription of the gene that codes for stromelysin-3. If this transcript is identified, then it is highly likely that the basement membrane separating cancerous cells and normal cells has been broken and the tissue has been invaded by cancerous cells.

The process is initiated by copying messenger RNA into complementary DNA. The complementary DNA is amplified for less than 35 cycles using a pair of specific oligonucleotide primers that give rise to a 449 base pair product for stromelysin-3 that have been specifically designed for this particular detection method and is then electrophoresed onto agarose gels to generate a population of single-stranded DNA. A DNA ladder from 100 base pairs to 1500 base pairs is also chromatographed for determining the size of the complementary DNA product. The single stranded DNA product is then compared to a size marker (449 bases) for stromelysin-3.

The present diagnostic method will allow for early detection, for example, of preneoplastic lesions such as adenomatous polyps or areas of dysplasia in ulcerative colitis. Such early detection allows treatment of the cancer to begin at initial stages of the disease, resulting in improved prognosis for the patient with cancer.

As discussed above, the present method for detecting cancer depends on detecting transcripts for the enzyme, stromelysin-3 (also known as matrix metalloproteinase-11), in human cells. The reverse transcriptase-polymerase chain reaction method utilized is more sensitive than other methods of enzyme identification such as Northern blotting or in-situ hybridization. Accordingly, the present diagnostic test allows for lower levels of cancer to be detected than with the other procedures.

The present method is also more cost effective as compared with currently used methods. Present methods sometimes require additional surgical procedures in order to confirm equivocal determinations. In addition, equivocal determinations sometimes result in the removal of the entire suspected organ instead of merely removal in portions.

Current methods such as endoscopic and colonoscopic examinations often require a physician to remove an amount of tissue from the sample of human tissue and then send it to a laboratory for diagnostic determinations. The current methods of detecting cancer are highly invasive and generally require large amounts of tissue in order to properly complete the diagnosis. These methods often require as much as 1 gram or more of tissue in order to obtain a proper test. The present test employs a chain reaction process wherein each cycle of polymerase chain reaction doubles the amount of gene present to produce amplified complementary DNA. This allows for diagnoses to be performed on very small amounts of tissue, on the order of 50 to 100 milligrams or less.

Broadly speaking, the diagnostic method involves extracting the messenger RNA from cells found in a sample of human tissue, fluids, or semi-fluids; reverse transcribing the messenger RNA into complementary DNA for stromelysin-3 by initiating the transcription using a pair of specific oligonucleotide primers that give rise to a 449 base pair DNA fragment for stromelysin-3 (the primers being designed so that the messenger RNA would yield a different size product from contaminating DNA); amplifying the complementary DNA by polymerase chain reaction for not more than about 35 cycles, and preferably 25 to 30 cycles; electrophoresing the amplified DNA onto agarose gels to determine whether stromelysin-3 was present in the cells. If the test for stromelysin-3 is positive, then cancerous cells in the sample are likely present.

Reverse transcriptase-polymerase chain reactions are becoming a widely used tool in various diagnostic areas. Because of the increasing popularity of using this method in other areas, its addition to a laboratory's repertoire of testing procedures could be an advantageous endeavor, having multiple applicability to other diagnostic tests. In summary, the capability of using this method as a means of detecting cancerous cells by the positive identification of stromelysin-3 could greatly increase the physician's ability to treat cancerous tumors prior to harmful progression.

DETAILED DESCRIPTION OF PREFERRED EMBODIMENT

The detection method of the present invention utilizes the technique of reverse transcriptase-polymerase chain reaction whereby messenger RNA is extracted from human cells and is then transcribed (or copied) into the complementary DNA for stromelysin-3. If the transcript of the gene that codes for stromelysin-3 is found using the methodology described, then it is highly likely that the tested cells indicate the tissue is cancerous.

The present diagnostic method involves extracting the messenger RNA from cells found in a sample of human tissue, fluids, or semi-fluids; reverse transcribing the messenger RNA into complementary DNA for stromelysin-3 by initiating the transcription using a pair of specific oligonucleotide primers that give rise to a 449 base pair DNA fragment for stromelysin-3 (the primers being designed so that the messenger RNA would yield a different size product from contaminating DNA); amplifying the complementary DNA by polymerase chain reaction for not more than about 35 cycles, and preferably 25 to 30 cycles; electrophoresing the amplified DNA onto agarose gels; and comparing it to standard positive and negative controls. If the test for stromelysin-3 is positive, then cancerous cells in the sample are likely present.

In addition, a control sample of normal non-cancerous tissue or fluids may be removed from the test patient and analyzed to confirm the findings. The control cells should be amplified for approximately the same number of chain reaction cycles because the control will likely show stromelysin-3 after about 45 cycles. Non-cancerous cells are not likely to exhibit stromelysin-3 even after 35 chain reaction cycles. In fact, 30 cycles is probably sufficient in most tests. However, 35 cycles should provide additional confirmation of the results.

Specifically, the diagnostic method involves the following steps:

(a) removing a sample of tissue, fluid, or semi-fluid to be tested for cancer from the human body;

(b) extracting the RNA from the cells in the sample;

(c) copying the messenger RNA from said portion into complementary DNA using reverse transcription;

(d) amplifying said complementary DNA by using a polymerase chain reaction that employs a pair of primers designed to allow the messenger RNA to give rise to a product having a size different from the size of a product produced by transcription of any contaminating genomic DNA, said reaction being run for less than a maximum of about 35 cycles so as to minimize false positive indications of the presence of stromelysin-3; and (e) examining said amplified complementary DNA to determine whether stromelysin-3 is present in said cells.

The present invention may be better understood by reference to the following examples:

EXAMPLES 1–13

Examples 1–13 are directed to an embodiment of the present invention wherein diagnostic tests are performed on human tissue found in the colon. Colectomies were performed on several patients. Tissue specimens were preserved in ice until the resected segment could be opened. A wedge of tissue (approximately 200 mg) was removed from the grossly non-necrotic area of the carcinoma. This included all tissue from the luminal surface to the serosa. A piece of normal colon (all layers) was taken 2–3 centimeters away from the carcinoma to be used for comparison as a control. Table 1 describes the extent of invasion and histopathologic diagnosis of the specimens. Preferably, the diagnostic testing is performed as soon as reasonably possible after removal of the tissue or the tissue should be preserved in ice or liquid nitrogen to delay degradation.

TABLE 1

| Example No. | Location | Dukes Stage | Histopathology |
|---|---|---|---|
| 1 | Right Colon | C1 | Mucinous |
| 2 | Rectosigmoid colon | C1 | Well differentiated |
| 3 | Liver metastasis | D | Moderately differentiated |
| 4 | Rectosigmoid colon | C2 | Well differentiated |
| 5 | Transverse colon | C2 | Moderately differentiated |
| 6 | Right colon | B1 | Moderately differentiated |
| 7 | Sigmoid colon | C1 | Well differentiated |
| 8 | Sigmoid colon | C1 | Moderately differentiated |
| 9 | Right colon | B1 | Well differentiated |
| 10 | Right colon | C1 | Moderately differentiated |
| 11 | Left colon | C1 | Moderately differentiated |
| 12 | Transverse colon | C1 | Moderately differentiated |
| 13 | Sigmoid colon | C1 | Moderately differentiated |

Total RNA was extracted from the normal or tumoral tissue with RNASTAT-60 (TEL-TEST "B" Inc., Friendswood (TX)), according to the manufacturer's directions (TEL-TEST "B" Bulletin No. 1). The quality of the total RNA extracted was verified by denaturing gel electrophoresis.

Oligonucleotide primers were designed with the program Oligo (National Biosciences, Inc., Plymouth, Minn.) using sequences obtained from Genbank and were synthesized by the University of South Carolina Institute for Biological Research and Technology. The amplification primers for β-actin (used as an internal control) were 5'CGTGGA-CATCCGCAAAGAC (SEQ ID: 4) and 5'CTCGGCCACAT-TGTGAACT (SEQ ID: 5), which give rise to a 484 bp product when messenger RNA is subjected to reverse transcriptase-polymerase chain reaction. The probe for blotting experiments was 5'AGGGTGTAACGCAACTAAG (SEQ ID: 6).

The amplification primers for stromelysin-3 were 5'TGGGTGTACGACGGTGAAAA (MP11-1), SEQ ID: 1, and 5'CATGGGTCTCTAGCCTGATA (MP11-2), SEQ ID: 2, which give rise to a 449 bp product for messenger RNA. The probe for blotting experiments was 5'CGCGCAG-GAAGTAGGCATAG (MP11-3), SEQ ID: 3. MMP11-1 corresponds to nucleotides 1096–1115 of the sense (messenger RNA) strand of Genbank X57766. MMP11-2 and MMP11-3 correspond to the complement of nucleotides 1363–1344 and 1544–1525 of Genbank X57766, respectively. The sequences amplified are within 1152 nucleotides of the poly (A) tail. Primer pairs closer to the poly (A) tail could not be designed due to limitations imposed by the requirement for a site at which an intron had been removed, and the necessity to design primers which should not give positive signals with unrelated messenger RNAs or with other metalloproteinase RNAs. The polymerase chain reaction primers were designed so that the messenger RNA would give rise to a product of a size different from any contaminating DNA, which would contain introns.

The messenger RNAs were copied into complementary DNA using a 25 µl reaction mix containing total cellular RNA (1 μg), oligo (dT)$_{15}$ (0.5 μg), 100 U RNAse H-minus Moloney murine virus reverse transcriptase (GIBCO BRL), 40 U RNAsin (Promega), 800 μM dATP, dCTP, dGTP, and dTTP, 2 mM DTT, 4 mM MgCl$_2$, 50 mM KC1 and 10 mM Tris.HC1, pH 8.3. The cellular RNA and oligo (dT)$_{15}$ (10 μl total volume) were heated at 65° C. for 3 min, cooled on ice and the remaining components added. The mix was then overlaid with 50 μl mineral oil (Sigma Chemical Co., Molecular Biology Grade) and incubated at 45° C. for 60 min. Each reaction mix was then diluted to 150 μl with glass distilled water and placed in a boiling water bath for 10 minutes to inactivate the reverse transcriptase.

Polymerase chain reaction was performed using the "hot start" technique in which reaction components are separated by a wax barrier so that no priming occurs under the less stringent conditions experienced at the beginning of the first step of polymerase chain reaction. The lower phase (25 μl) contained 10 mM Tris.HC1, pH 8.3, 6 mM MgCl$_2$, 800 μM dATP, dCTP, dGTP and dTTP, and 10 pmol of each primer. A 45 μl wax bead (15) (Ameraffin, Baxter S P, McGaw Park, Ill.) was added, the tube was heated briefly at 70° C. to melt the wax and cooled (but not below 0° C.) to allow the wax to set. The upper phase (75 μl total) was then added, this contained 67 mM KC1, 13 mM Tris.HC1, pH 8.3, Taq polymerase (2.5 U) and 5 μl of the diluted reverse transcription mix (which was heated for 5 min in a boiling water bath and then quickly cooled in an ice-water bath immediately before use). This was subjected to a 2.5 min time delay step at 95° C. in a Perkin Elmer Thermocycler, followed by 20–45 cycles of polymerase chain reaction (95° C. for 1 min, 58° C. for 1 min, 72° C. for 1 min), a 10 min incubation at 72° C., and then an indefinite incubation at 4° C.). The products were separated on Metaphor (FMC Bioproducts, Rockland, Me.) agarose gels.

All polymerase chain reaction experiments included control reactions which contained all components except complementary DNA. No band was ever detectable in these control reactions. β-actin primers were run as a control. β-actin is merely an internal control to ensure that RNA sample remains intact. Other controls could also be used with the present inventive technique. The RNA competitive reference standard (RNA-CRS) described later is an example of one such control.

Polymerase chain reaction products were sequenced as known in the art to ensure that the molecules created by the process were, in fact, identical to known sequences of stromelysin-3. Briefly, one-tenth of the polymerase chain reaction product was amplified in an asymmetric chain reaction to generate a population of single-stranded DNA which was then directly sequenced using Sequenase (United States Biochemical Corp., Cleveland, Ohio). The sequence of the products was then compared with the published sequences from Genbank.

The total RNA extracted from human colon tissue was subjected to reverse transcriptase-polymerase chain reaction using the amplification primers for either β-actin or stromelysin-3 (METALLOPROTEINASE-11). For each primer set, only a single band, which was of the predicted size, was seen upon analysis by Metaphor agarose gel electrophoresis, even if the polymerase chain reaction was carried out for 45 cycles.

Southern blotting followed by probing with an internal oligonucleotide probe indicated that a single band of the correct size was specifically recognized by the appropriate internal probe. To further confirm that these bands corresponded to the correct sequence, one set of such polymerase chain reaction products was amplified by asymmetric polymerase chain reaction to generate single-stranded DNA which was directly sequenced to obtain the consensus sequence of the total product. The sequence was compared to sequences deposited at Genbank and confirmed that the correct region of the appropriate mRNA was amplified by each pair of external primers.

The amplification primers for β-actin were designed so that they spanned one exon/exon boundary, thus any amplification products due to contamination by genomic DNA (which would contain the intron) would be considerably larger than those from messenger RNA.

The predicted sites of introns were determined by comparison of the metalloproteinase-11 sequence to metalloproteinase-1, -2, -3 and -9, and primers were designed accordingly. It was anticipated that two introns should occur in the genomic DNA region spanned by primers MP11-1 and MP11-2. The same two introns would be expected to occur in the region amplified if MP11-1 and MP11-3 were used for polymerase chain reaction of DNA. The metalloproteinase-11 specific primer pairs (MP11-1/MP11-2) and (MP11-1/MP11-3) were used to amplify RNA and obtain a single band corresponding to 449 or 268 base pairs, respectively, as expected for the messenger RNA. When these primer pairs were used in reverse transcriptase-polymerase chain reaction, but the reverse transcriptase was omitted, no product corresponding to 449 or 268 base pairs was seen, indicating that these bands were dependent on reverse transcriptase, and, therefore, arose from RNA. However, in each case a single band was seen, at approximately 1450 base pairs and 1270 base pairs respectively. This band was presumably due to genomic DNA contamination. Thus, this region of the gene apparently contains intron(s) totaling approximately 1000 base pairs. When the band at 1450 nucleotides amplified using MP11-1/MP11-2 was subjected to Southern blotting and probed with MP11-3, it hybridized, suggesting that it was metalloproteinase-11 DNA and not due to amplification of a non-specific region of the DNA. The genomic sequence of this gene has been reported and is consistent with the above data since the DNA in this region contains a single intron of 928 base pairs following the nucleotide corresponding to nucleotide 1342 of Genbank X57766. Thus, for all the amplification primers, the polymerase chain reaction product corresponding to RNA can be readily distinguished from any band arising from genomic DNA contamination.

Reverse transcriptase-polymerase chain reaction was performed on RNA extracted from colon adenocarcinoma tissue and normal tissue from an adjacent region of the colon as described above except where hereinafter indicated on the 12 patients listed in Table 1. In addition, one case (Table 1, #3) was from a patient from whom the tissue was a micrometastasis obtained by liver biopsy. With the β-actin primers, a band at the expected position was visible by ethidium bromide staining after 20 cycles and appeared to be of similar intensity in all. A similar pattern, although with more intensely stained bands, was seen after 25 cycles. With the metalloproteinase-11 amplification primers, faint bands were seen in all but case #3 when the adenocarcinoma samples were subjected to 25 cycles. A similar pattern, but with more intensely stained bands, was seen after 30 cycles.

These results suggest that the ratio of metalloproteinase-11 messenger RNA relative to β-actin messenger RNA is considerably higher in the primary adenocarcinoma samples compared to normal colon samples from the same patients. The only case where no amplification of metalloproteinase-11 transcripts was obtained after 25 or 30 cycles of polymerase chain reaction was #3. This observation was reproducible in independent reverse transcriptase-polymerase chain reactions. Results from different cycle numbers indicated that even though the actin messenger RNA signal may have been slightly lower in this sample, if the same level of stromelysin-3 messenger RNA relative to actin messenger RNA were present in this sample as in the other tumors, then a stromelysin-3 band should have been readily detectable after 30 cycles. In case #3, RNA was extracted from the biopsy of a micrometastasis of a rectal adenocarcinoma to the liver. The histopathologic examination of this lesion indicated the present of only a few carcinoma cells with essentially no stromal reaction, thus accounting for the negative diagnosis.

Thus, by using polymerase chain reaction with appropriately designed primers, a marked increase in transcripts for stromelysin-3 (metalloproteinase-11) can be detected in primary colorectal adenocarcinomas compared to normal colon tissue from the same patients. This is shown by the fact that, in samples which give similar signals with β-actin primers, the stromelysin-3 signal was detectable in all twelve primary adenocarcinoma tissues examined after 25 cycles of polymerase chain reaction. However, in the normal tissue, even after 30 cycles of polymerase chain reaction, no stromelysin-3 was detectable. There were low amounts of stromelysin-3 transcripts present in the normal colon tissue after about 45 cycles of polymerase chain reaction.

Others have reported that stromelysin-3 expression is often elevated in adenocarcinomas using Northern blot or in situ hybridization techniques and have suggested that elevated stromelysin-3 levels are associated with the malignant stages of colorectal cancer. Using Northern blot analysis, Urbanski et al. did not find stromelysin-3 messenger RNA in normal colon tissue, in mildly dysplastic adenomas, or in most cases of moderately dysplastic adenoma. Using in situ hybridization, Okada et al. and Newell et al. reported that all adenomas were negative, although most carcinomas were positive. The more sensitive reverse transcriptase method can detect low levels of stromelysin-3 messenger present in adjacent colon tissues which are not detectable by the less sensitive Northern or in situ hybridization methods. This tissue may not truly be normal since it also comes from a subject with cancer.

In another embodiment of the present invention, a means is disclosed for evaluating the colon for the possible presence of cancer that eliminates the need for a colonoscopy. Instead, an enema is used for ultimately collecting fluids and sloughed cells from the intestine. The presently disclosed RT-PCR detection process is so sensitive that even cancerous cells diluted during such extraction may be detected.

Lesions at either end of the gastrointestinal (GI) tract include pre-neoplastic lesions, i.e., those with the potential to progress to cancer. These pre-neoplastic lesions are the so-called neoplastic polyps and pseudopolyps associated with ulcerative colitis that arise near the distal end of the GI tract, and Barrett's esophagus (epithelial metaplasia and dysplasia associated with chronic gastric reflux) near the proximal end. In order to prevent the progression of these lesions to full-blown cancer, a means of early identification of the cancerous potential of these lesions must be available to clinicians in order that appropriate intervention can be initiated to abort the progression to cancer. The present invention allows early detection of cancerous cells by recognizing the high degree of correlation between adenocarcinoma of the colon and the increased messenger RNA encoding a matrix metalloproteinase, stromelysin-3.

When metalloproteinases degrade components of the extracellular basement membrane, metastasis is initiated which frees the neoplastic cells from their physical constraints and permits them to enter first into the extracellular space, then into the lymphatics and finally into other sites of the body during the metastatic process. Quantitative differences are determined by the recently described technique of preparing an RNA competitive reference standard (RNA-CRS) template with internal nucleotide deletions without plasmid vectors. Reidy, M C, Timm, Jr., E A and Stewart, C C: Quantitavie RT-PCR for Measuring Gene Expression, Biotechniques Vol. 18: 70–76, 1995. The rationale for determining the degree of amplification of stromelysin-3 in carcinomas and pre-neoplastic proliferative lesions comes from the observations (1) that stromelysin-3 is expressed in the stroma of a number of tissues during development and remodeling and (2) of the rapid turnover of the colonic mucosa, including the pericryptal fibroblast sheath.

By employing the present invention, preneoplastic lesions of the gastrointestinal tract are examined to determine whether enhanced expression of stromelysin-3 occurs at this earlier stage in the neoplastic sequence. Examination of a pseudopolyp from a patient with ulcerative colitis shows enhanced expression. In addition, the present invention may be employed as a non-invasive screening test for proliferative, and therefore potentially neoplastic, lesions of the gastrointestinal tract. This allows for screening of asymptomatic persons for their risk of developing cancer of the gastrointestinal tract using a low cost, easily administered, highly sensitive and highly specific test. As an example, a laboratory test using RT-PCR may cost between $70 and $100, which is considerably less than one that requires the time and expertise of a physician for interpretation (as much as $2,000). In addition, the discomfort of colonoscopy, the current method by which the colon is examined and tissue is retrieved for diagnosis, could be limited to those patients at greatest risk. Presently, diagnosis depends on markers that are diverse, may not be positive, and are neither as sensitive or specific as RT-PCR. These include family history, results of fecal occult blood test, several biochemical tests and the histologic features of pre-neoplastic adenomatous polyps.

The present test examines the pre-neoplastic lesions of both the esophagus and colon in order to determine whether or not stromelysin-3 expression is enhanced at a much earlier stage in the neoplastic process, thus permitting earlier intervention, less discomfort and lower cost to the patient. Use of the sensitive method of RT-PCR employs the primers described that are specific for this enzyme.

The presently described non-invasive test for pre-neoplastic and neoplastic lesions of the colon is based on the following theses. The daily loss of mucosal cells due to sloughing into the lumen and excretion is of the order of $10^{10}$ normal cells per day. A tumor of 1 $cm^3$ could conceivably shed this number of cells. Studies of the pericryptal fibroblast layer of the intestine indicate that maturation parallels that of the mucosa. While the fate of the mucosal epithelium is clear, the fate for the pericryptal fibroblasts is unknown. Review of electron micrographs and diagrams strongly suggests that the only barrier to escape could be penetrated due to release of matrix metalloproteinases, because the basement membrane is constructed in such a way that cells can percolate through it.

Although the method is described with respect to the colon, other potentially cancerous regions of the body may also be examined using this method.

EXAMPLE 14

The diagnostic test for colonic polyps that have the potential of carcinoma development is undertaken by looking for enhanced expression of the transcript for stromelysin-3 as described above. Polyps of the histologic types, villous adenoma or tubulovillous adenoma, as well as non-neoplastic polyps (hyperplastic) are obtained endoscopically and are processed in the same manner as described with samples of colon cancer. The polyp collecting is done according to protocol 18070-E180 approved by the University of South Carolina's Human Studies Committee. The removed polyp is placed in a sterile tube which contains Hanks' solution and placed in a refrigerator at 4° C. The specimen is then brought to the laboratory where it is frozen in liquid nitrogen until extraction of m-RNA and RT-PCR. Simultaneously, the fluid contents of the colon obtained following an enema preparative to the colonoscopy collected in the trap attached to the side arm of the colonoscope, without washing out the lumen with tap water (which would lyse cells). This fluid is then transferred to a 50 ml tube, poured through a 70μ cell strainer (Falcon), and drawn up in a 20 ml syringe. It is then passed serially through a 19 gauge and a 22 gauge needle in order to break up food material and prepare a single cell suspension of cells. The sample is then placed in a mega-funnel attached to a cytospin slide precoated with fibronectin. The cytospin tube is centrifuged at 1400 rpm for 8 minutes. The fluid remaining in the mega-funnel is decanted and the slide is placed in 5 ml of RNA STAT 60. The quantity of RNA is determined as described above and RT-PCR started. Quantitation of specific mRNA encoding stromelysin-3 may be accomplished by comparing the specific RNA to an internal RNA competitive reference standard (RNA-CRS). The RNA-CRS is identical to the sequence of stromelysin-3 mRNA except for the deletion of 80 bases.

The technique for quantitative RT-PCR is as follows. The RNA-CRS is designed using the fact that there is a 45-mer downstream primer that is complementary to stromelysin-3 mRNA. The initial 25 bases starting from the 5' end of the primer are 80 bases downstream on the message in relation to the next 20 bases at the 3' end if the primer. Thus the 80-base deletion in the final PCR product is produced. The 45-mer upstream primer (5'→3') is identical in sequence to the mRNA strand except that the 5' end of the primer contains 25 bases which codes for the binding region of the $T_7$ RNA polymerase.

Total RNA is added to an RT reaction mixture containing mM dNTPs, DTT SUPERSCRIPT RNase H-RT, RNAsin, and Tris buffer. The protocol for heating and cooling will follow that described in Johnson, L D, Hunt, D M, Kim, K, Nachtigal, M: Amplification of Stromelysin-3 Transcripts from Carcinomas of the Colon, Human Pathol. 27:964–968, 1990. The cDNA produced now contains the T7 polymerase promoter and it has an 80 base deletion and can be easily identified when co-chromatographed on agarose gels.

The expression of stromelysin-3 transcript in the preneoplastic polyps should fall between the number of cycles of PCR required for identification of carcinoma (20 or 25) and normal colon ($\geq 45$). From these data, it can be seen that the messengers encoding enzymes involved in cell turnover, including the messenger for stromelysin-3, is expressed in an enhanced manner. Unlike other markers which are the result of gene mutations, deletions or multiplication, and therefore not positive in every case, stromelysin-3 is expressed in an enhanced manner in generally every case.

EXAMPLE 15

Another embodiment of the present invention involves individual matrix cells that are programmed to stimulate the growth and spread of cancer cells, viz. the pericryptal fibroblasts of the colon. There is a generally held opinion that DNA, but not RNA, can be extracted from feces due to the great abundance of bacterial ribonucleases present. Sidransky, et al. reported the identification of ras oncogene mutations by extracting DNA from the stools of patients. Sidransky, D, Tokino, T. Hamilton, S R, Kinzler, K W, Levin, B, Frost, P, Vogelstein, B: Identification of ras oncogene mutations in the stool of patients with curable colorectal tumors' Science 256:102–105, 1992. The use of RNA rather than DNA eliminates a number of problems in interpretation because it is a measure of expression. For that reason, RT-PCR is a far more specific method of diagnosis and may be used in this method for non-invasively detecting cancer based on stool samples taken from patients.

Although preferred embodiments of the invention have been described using specific terms, devices, concentrations, and methods, such description is for illustrative purposes only. The words used are words of description rather than of limitation. It is to be understood that changes and variations may be made without departing from the spirit or the scope of the following claims.

What is claimed is:

1. A rapid method for detecting the existence of cancerous cells by using cycles of a reverse transcriptase polymerase chain reaction to determine whether stromelysin-3 is present in the cells of a sample taken from the gastrointestinal tract, said method comprising the steps of:
   a) removing a sample of fluids or semi-fluid to be tested for cancer from the gastrointestinal tract, said sample containing cells having messenger RNA;
   b) extracting said messenger RNA from said cells in said sample;
   c) copying said messenger RNA from said cells into complementary DNA using reverse transcription;
   d) amplifying said complementary DNA by using a polymerase chain reaction that employs a pair of primers designed to allow the messenger RNA to give rise to a product having a size different from the size of a product produced by transcription of any contaminating genomic DNA, said reaction being run for less than a maximum of about 35 cycles so as to minimize false positive indications of the presence of stromelysin-3; and
   e) detecting whether stromelysin-3 is expressed in said amplified complementary DNA, wherein the expression of stromelysin-3 in said amplified complementary DNA is indicative of the presence of cancerous cells in the gastrointestinal tract.

2. The method of claim 1, wherein said pair of primers are 5'TGGGTGTACGACGGTGAAAA (MP11-1), SEQ ID: 1, and 5'CATGGGTCTCTAGCCTGATA (MP11-2), SEQ ID: 2.

3. The method of claim 1, wherein said sample is fluid removed from the colon.

4. The method of claim 1, wherein said sample is fluid collected after an enema.

5. The method of claim 1, wherein said sample is feces.

6. The method of claim 1, wherein said sample is fluid extracted or excreted from the human body.

7. The method of claim 1, wherein said sample is semi-fluid extracted or excreted from the human body.

8. The method of claim 1, wherein said rapid method is completed within twenty-four hours.

9. The method of claim 1, wherein said polymerase chain reaction is run for 30 cycles.

10. A rapid method for detecting the expression of stromelysin-3 in pre-neoplastic polyps in the gastrointestinal tract by using cycles of a reverse transcriptase polymerase chain reaction to determine whether stromelysin-3 is present in the cells of a sample taken from the gastrointestinal tract, said method comprising the steps of:
   a) removing a sample of fluids or semi-fluid to be tested for cancer from the gastrointestinal tract, said sample containing cells having messenger RNA;
   b) extracting said messenger RNA from said cells in said sample;
   c) copying said messenger RNA from said cells into complementary DNA using reverse transcription;
   d) amplifying said complementary DNA by using a polymerase chain reaction that employs a pair of primers designed to allow the messenger RNA to give rise to a product having a size different from the size of a product produced by transcription of any contaminating genomic DNA, said reaction being run for less than a maximum of about 35 cycles so as to minimize false positive indications of the presence of stromelysin-3; and
   e) detecting whether stromelysin-3 is expressed in said amplified complementary DNA, wherein the expression of stromelysin-3 in said amplified complementary DNA is indicative of the presence of pre-neoplastic polyps in the gastrointestinal tract.

11. The method of claim 10, wherein said pair of primers are 5'TGGGTGTACGACGGTGAAAA (MP11-1) and 5'CATGGGTCTCTAGCCTGATA (MP11-2).

12. The method of claim 10, wherein said sample is fluid removed from the colon.

13. The method of claim 10, wherein said sample is fluid collected after an enema.

14. The method of claim 10, wherein said sample is feces.

15. The method of claim 10, wherein said sample is fluid extracted or excreted from the human body.

* * * * *

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other Nucleic Acid
      (A) DESCRIPTION: Oligonucleotide primer (iii) HYPOTHETICAL: No (iv) ANTI-SENSE: No (vi) ORIGINAL SOURCE: Genbank X577-66

(vii) IMMEDIATE SOURCE: synthesized at the University of South
                               Carolina (viii) POSITION IN GENOME:
             (C) UNITS:  NT 1096-1115 of the sense (mRNA) strand (ix) FEATURE:
             (D) OTHER INFORMATION:  within 1152 NT of poly (A) tail (x) PUBLICATION INFORMATION:
             (A) AUTHORS: Johnson, Lewis D., Hunt, D. Margaret, Kim,
                          Koanhoi, and N
             (B) TITLE: Amplification of Stromelysin-3 Transcripts from
                        Carcinomas of the colon
             (C) JOURNAL: Human Pathology
             (D) VOLUME: 27
             (E) ISSUE: 9
             (F) PAGES:    964-968
             (G) DATE: SEPT-1996
             (K) RELEVANT RESIDUES IN SEQ ID NO:1: FROM 1096 TO 1115

(xi) SEQUENCE DESCRIPTION:  SEQ ID NO: 1:

TGGGTGTACG ACGGTGAAAA                                                  20

(2) INFORMATION FOR SEQ ID NO: 2:

(i) SEQUENCE CHARACTERISTICS:
             (A) LENGTH: 20 base pairs
             (B) TYPE: Nucleic acid
             (C) STRANDEDNESS:  Single
             (D) TOPOLOGY: Linear (ii) MOLECULE TYPE: Other Nucleic Acid
             (A) DESCRIPTION: Oligonucleotide primer (iii) HYPOTHETICAL: No (iv) ANTI-SENSE:  Yes (vi) ORIGINAL SOURCE: Genbank X577-66

(vii) IMMEDIATE SOURCE: synthesized at the University of South
                               Carolina (viii) POSITION IN GENOME:
             (C) UNITS:  NT 1363-1344

(ix) FEATURE:
             (D) OTHER INFORMATION:  within 1152 NT of poly (A) tail (x) PUBLICATION INFORMATION:
             (A) AUTHORS: Johnson, Lewis D., Hunt, D. Margaret, Kim,
                          Koanhoi, and Nachtigal, Maurice
             (B) TITLE:  Amplification of Stromelysin-3 Transcripts from
                         Carcinomas of the Colon
             (C) JOURNAL:  Human Pathology
             (D) VOLUME: 27
             (E) ISSUE: 9
             (F) PAGES: 964-968
             (G) DATE: SEPT-1996
             (K) RELEVANT RESIDUES IN SEQ ID NO:2: FROM 1363 TO 1344

(xi) SEQUENCE DESCRIPTION:  SEQ ID NO: 2:

CATGGGTCTC TAGCCTGATA                                                  20

(2) INFORMATION FOR SEQ ID NO:3:

(i) SEQUENCE CHARACTERISTICS:
             (A) LENGTH: 20 base pairs
             (B) TYPE: Nucleic acid (C) STRANDEDNESS: Single
        (D) TOPOLOGY: Linear (ii) MOLECULE TYPE: Other Nucleic Acid
        (A) DESCRIPTION: Oligonucleotide probe (iii) HYPOTHETICAL: No (iv) ANTI-SENSE: Yes (vi) ORIGINAL SOURCE: Genbank X577-66

(vii) IMMEDIATE SOURCE: synthesized at the University of South
                    Carolina (viii) POSITION IN GENOME:
        (C) UNITS: NT 1544-1525

(ix) FEATURE:
        (D) OTHER INFORMATION: within 1152 NT of poly (A) tail (x) PUBLICATION INFORMATION:
        (A) AUTHORS: Johnson, Lewis D., Hunt, D. Margaret, Kim,
                Koanhoi, and Nacht
        (B) TITLE: Amplification of Stromelysin-3 Transcripts from
                Carcinomas of the colon
        (C) JOURNAL: Human Pathology
        (D) VOLUME: 27
        (E) ISSUE: 9
        (F) PAGES: 964-968
        (G) DATE: SEPT-1996
        (K) RELEVANT RESIDUES IN SEQ ID NO:3: FROM 1544 TO 1525

(xi) SEQUENCE DESCRIPTION: SEQ ID NO: 3:

CGCGCAGGAA  GTAGGCATAG                                               20

(2) INFORMATION FOR SEQ ID NO:4:

(i) SEQUENCE CHARACTERISTICS:
        (A) LENGTH: 19 base pairs
        (B) TYPE: Nucleic acid
        (C) STRANDEDNESS: Single
        (D) TOPOLOGY: Linear (ii) MOLECULE TYPE: Other Nucleic Acid
        (A) DESCRIPTION:   -actin primer (iii) HYPOTHETICAL: No (iv) ANTI-SENSE: No (vi) ORIGINAL SOURCE: Genbank X00351 (originally designed from 04
                            August 1986 file)
  (vii) IMMEDIATE SOURCE: synthesized at the University of South
                    Carolina (viii) POSITION IN GENOME:
        (C) UNITS: NT 899-917 (position in 25 May 1997 file version)

(ix) FEATURE:
        (D) OTHER INFORMATION: primer designed from sequence as listed
                    in 04 August 1986 Genbank file.

(x) PUBLICATION INFORMATION:
        (A) AUTHORS: Johnson, Lewis D., Hunt, D. Margaret, Kim,
                Koanhoi, and Nacht
        (B) TITLE: Amplification of Stromelysin-3 Transcripts from
                Carcinomas of the colon
        (C) JOURNAL: Human Pathology
        (D) VOLUME: 27
        (E) ISSUE: 9
        (F) PAGES: 964-968
        (G) DATE: SEPT-1996
        (K) RELEVANT RESIDUES IN SEQ ID NO:4: NT 899-917 (position
                according to 25 May 1997 file version)
   (xi) SEQUENCE DESCRIPTION: SEQ ID NO: 4:

CGTGGACATC  CGCAAAGAC                                                19

```
(2) INFORMATION FOR SEQ ID NO:5:

(i) SEQUENCE CHARACTERISTICS:
        (A) LENGTH: 19 base pairs
        (B) TYPE: Nucleic acid
        (C) STRANDEDNESS: Single
        (D) TOPOLOGY: Linear (ii) MOLECULE TYPE: Other Nucleic Acid
        (A) DESCRIPTION:  -actin primer (iii) HYPOTHETICAL: No (iv) ANTI-SENSE: complementary to file sequence (vi) ORIGINAL SOURCE: Genbank X00351 (originally designed from 04
                         August 1998)

(vii) IMMEDIATE SOURCE: synthesized at the University of South
                          Carolina (viii) POSITION IN GENOME:
        (C) UNITS: NT 1382-1364 (position in 25 May 1997 file version)

(ix) FEATURE:
        (D) OTHER INFORMATION:   primer designed from sequence as
                         listed in 04 August 1986 Genbank file.

(x) PUBLICATION INFORMATION:
        (A) AUTHORS: Johnson, Lewis D., Hunt, D. Margaret, Kim,
                     Koanhoi, and Nacht
        (B) TITLE: Amplification of Stromelysin-3 Transcripts from
                   Carcinomas of
        (C) JOURNAL: Human Pathology
        (D) VOLUME: 27
        (E) ISSUE: 9
        (F) PAGES: 964-968
        (G) DATE: SEPT-1996
        (K) RELEVANT RESIDUES IN SEQ ID NO:5: NT 1382-1364 (position          according (xi) SEQUENCE DESCRIPTION: SEQ ID NO: 5:

CTCGGCCACA TTGTGAACT                                         19

(2) INFORMATION FOR SEQ ID NO:6:

(i) SEQUENCE CHARACTERISTICS:
        (A) LENGTH: 19 base pairs
        (B) TYPE: Nucleic acid
        (C) STRANDEDNESS: Single
        (D) TOPOLOGY: Linear (ii) MOLECULE TYPE: Other Nucleic Acid
        (A) DESCRIPTION:   -actin probe (iii) HYPOTHETICAL: No (iv) ANTI-SENSE: complementary to file sequence (vi) ORIGINAL SOURCE: Genbank X00351 (originally designed from 04
                         August 1998)

(vii) IMMEDIATE SOURCE: synthesized at the University of South
                          Carolina (viii) POSITION IN GENOME:
        (C) UNITS: NT 1199-1181 (position in 25 May 1997 file version)

(ix) FEATURE:
        (D) OTHER INFORMATION: probe designed from sequence as listed
                         in 04 August 1986 Genbank file.

(x) PUBLICATION INFORMATION:
        (A) AUTHORS: Johnson, Lewis D., Hunt, D. Margaret, Kim,
                     Koanhoi, and Nachtigal, Maurice
        (B) TITLE: Amplification of Stromelysin-3 Transcripts from
                   Carcinomas of of the colon
```

```
        (C) JOURNAL: Human Pathology
        (D) VOLUME: 27
        (E) ISSUE: 9
        (F) PAGES: 964-968
        (G) DATE: SEPT-1996
        (K) RELEVANT RESIDUES IN SEQ ID NO:6: NT 1199-1181 (position
            according to 25 May 1997 file version)

(xi) SEQUENCE DESCRIPTION:  SEQ ID NO: 6:

AGGGTGTAAC GCAACTAAG                                            19
```